United States Patent
Hughes

(10) Patent No.: US 7,455,997 B2
(45) Date of Patent: Nov. 25, 2008

(54) PRODUCTION OF FERMENTATION PRODUCT

(75) Inventor: Jonathan Hughes, Huddersfield (GB)

(73) Assignee: Ciba Specialty Chemicals Water Treatments Ltd, West Yorkshire, Bradford (GB)

( * ) Notice: Subject to any disclaimer, the term of this patent is extended or adjusted under 35 U.S.C. 154(b) by 718 days.

(21) Appl. No.: 10/523,302

(22) PCT Filed: Jul. 28, 2003

(86) PCT No.: PCT/EP03/08291

§ 371 (c)(1),
(2), (4) Date: Jan. 31, 2005

(87) PCT Pub. No.: WO2004/015145

PCT Pub. Date: Feb. 19, 2004

(65) Prior Publication Data

US 2005/0233031 A1   Oct. 20, 2005

(30) Foreign Application Priority Data

Aug. 5, 2002   (GB)   ................... 0218019.8

(51) Int. Cl.
C12P 13/20   (2006.01)

(52) U.S. Cl. ................ 435/109; 127/37; 127/55; 127/56; 210/609; 210/702; 210/710; 210/725; 210/727; 210/728; 426/49; 426/495; 435/106; 435/139; 435/140; 435/141; 435/144; 435/145; 435/146; 435/150; 435/159; 435/160; 435/163; 435/166; 435/171

(58) Field of Classification Search .............. 210/728; 435/163
See application file for complete search history.

(56) References Cited

U.S. PATENT DOCUMENTS

| | | | | |
|---|---|---|---|---|
| 3,711,462 A * | 1/1973 | Abdo | ........... | 536/123 |
| 4,384,897 A | 5/1983 | Brink | ........... | 127/37 |
| 4,525,218 A | 6/1985 | Chen et al. | ........... | 127/37 |
| 5,215,902 A * | 6/1993 | Tedder | ........... | 435/161 |
| 5,529,699 A | 6/1996 | Kuo et al. | ........... | 210/735 |
| 5,536,325 A * | 7/1996 | Brink | ........... | 127/43 |
| 5,628,830 A | 5/1997 | Brink | ........... | 127/36 |
| 5,705,369 A | 1/1998 | Torget et al. | ........... | 435/105 |
| 6,071,417 A * | 6/2000 | Adachi | ........... | 210/723 |
| 6,130,303 A * | 10/2000 | Neff et al. | ........... | 526/306 |
| 6,132,625 A * | 10/2000 | Moffett | ........... | 210/727 |
| 6,967,085 B1 * | 11/2005 | Hughes et al. | ........... | 435/29 |

FOREIGN PATENT DOCUMENTS

| | | |
|---|---|---|
| DE | 3107950 | 9/1982 |
| EP | 0102759 | 3/1984 |
| EP | 0150933 | 8/1997 |
| GB | 2017707 | 10/1979 |
| JP | 61204100 | 9/1986 |
| WO | 94/29475 | 12/1994 |
| WO | 99/50195 | 10/1999 |
| WO | 01/34908 | 5/2001 |

OTHER PUBLICATIONS

Y Kholkin et al., Applied Biochemistry and Biotechnology, vol. 82, No. 2, pp. 135-140 (1999).
Derwent Abstr. 1993-150324 for SU 1733477 (1992).
Derwent Abstr. 1997-488205 for RU 2077594 (1997).
Tucker et al., Applied Biochemistry and Biotechnology, vol. 70-72, No. 0, (1998), pp. 25-35.
Shell et al., Applied Biochemistry and Biotechnology, vol. 70-72, No. 0, (1998), pp. 17-24.
Derwent Abstr. 1982-79144E [38] for DE 3107950 (1982).
Derwent Abstr. 1986-281090 [43] for JP 61204100 (1986).
Kim et al., Applied Biochemistry and Biotechnology, vol. 91-93, (2001), pp. 253-267.
NREL/TP-580-26157, Jul. 1999, "Lignocellulosic Biomass to Ethanol Process Design and Economics Utilizing Co-Current Dilute Acid Prehydrolysis and Enzymatic Hydrolysis Current and Futuristic Scenarios".
Stenberg et al., Applied Biochemistry and Biotechnology, vol. 70-72, (1998), pp. 697-708.

Chem. Abstr. 1985:185565 for Makromolekulare Chemie, (1985), vol. 186, No. 2, pp. 273-281.

* cited by examiner

*Primary Examiner*—Peter A. Hruskoci
(74) *Attorney, Agent, or Firm*—Shiela A. Loggins

(57) ABSTRACT

A process of producing fermentation product comprising the steps of, (i) forming an acidified suspension of particulate plant derived material comprising a first polysaccharide which is more readily hydrolysable and a second polysaccharide which is more difficult to hydrolysable, (ii) allowing the first polysaccharide to undergo hydrolysis by action of the acid at a temperature of at least 50° C. under conditions such that the first polysaccharide is hydrolysed and thereby forming a mixture of an aqueous liquor containing dissolved sugar and a solid residue containing the second polysaccharide, (iii) subjecting the mixture to one or more separation stages in which the solid residue and aqueous sugar liquor are substantially separated from each other, (iv) optionally washing the residue substantially free of acid and sugar, (v) adjusting the pH of the aqueous liquor to at least 4, (vi) passing the aqueous liquor from step (iv) into a fermentation stage where the dissolved sugars are acted upon by a microorganism in a fermentation broth to produce a fermentation product, (vii) contacting the second polysaccharide by an enzyme, said enzyme hydrolyses the second polysaccharide to the component sugars, and allowing the component sugars to be acted upon by a microorganism in the fermentation broth to produce the fermentation product, (viii) separating the fermentation product from the broth, characterised in that the separation stage(s) in step (iii) is/are assisted by flocculation of the solid by-product, employing one or more flocculating agent(s) selected from the group consisting of water soluble polymers, water swellable polymers and charged microparticulate material. Typically such fermentation products include for instance ethanol, glycerol, acetone, n-butanol, butanediol, isopropanol, butyric acid, methane, citric Acid, fumaric acid, lactic acid, propionic acid, succinic acid, itaconic acid, acetic acid, acetaldehyde, 3-hydroxypropionic acid, glyconic acid, tartaric acid and amino acids such as L-glutaric acid, L-lysine, L-aspartic acid, L-tryptophan, L-arylglycines or salts of any of these acids.

22 Claims, 4 Drawing Sheets

PRODUCTION OF FERMENTATION PRODUCT

The present invention relates to processes of treating plant derived material to provide an aqueous liquor containing sugars which are used in a fermentation process to produce a fermentation product. Typically such fermentation products include for instance ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid, tartaric acid and amino acids such as L-glutaric acid, L-lysine, L-aspartic acid, L-tryptophan, L-arylglycines or salts of any of these acids. It is known to treat a biomass with acid in order to hydrolyse polysaccharides to the component sugars that can be used in a fermentation process to produce a fermentation product. For instance U.S. Pat. No. 4,384,897 describes a method of treating biomass material in which it is subjected to a two stage hydrolysis in which polysaccharides that are more easily hydrolysed, such as hemicellulose and then in a second stage the more difficult to depolymerise material e.g. cellulose, is depolymerised using a more severe hydrolytic treatment. The products of the first and second stages include sugar solutions, organic acids and aldehydes. The monosaccharides are subjected to fermentation to produce ethanol and the beer resulting from the fermentation may then be subjected to rectification to produce ethanol of commercial grade. U.S. Pat. No. 4,384,897 sets out to provide improvements in the more efficient washing of solids, the use of co-current washing or countercurrent washing of solids and proposes the use of ferric and or aluminum ions as flocculating agents to separate finely dispersed solids resulting from the neutralisation of the hydrolysate liquor stream.

Kyoung Heon Kim et al (Applied Biochemistry and Biotechnology, Vol 91-93, pg 253-267) investigates the continuous countercurrent hydrolysis and extraction of hemicellulose from acid pretreated wood residues and considers the effect on drainage rate of such a pretreated biomass. A continuous countercurrent screw extractor used relies on the percolation of water by gravity through the pretreated biomass. One difficulty identified is that the pretreated biomass has poor water drainage properties and channelling or blockage may occur inside the extractor, which can result in low sugar recovery or low throughput.

It would be desirable to improve the drainage properties of acid treated plant derived material in order to maximise sugar recovery.

It is also known from National Renewable Energy Laboratory (NREL) report entitled "Lignocellulose Biomass to Ethanol Process Design and Economics of Co-Current Dilute Acid Prehydrolysis and Enzymatic Hydrolysis Current and Future Scenarios" NREL/IP-580-26157 (July 1999) to treat cellulose as the second polysaccharide by a cellulase enzyme in order to hydrolyse the cellulose into its component sugars. In one form of this process the solid by-product residue resulting from the first hydrolysis step and containing cellulose is divided into a main stream and a secondary stream. The main stream is fed directly into the fermentation vessel and the secondary stream is passed to a cellulase production stage, in which fungi are allowed to grow and act upon the cellulose, such that sugars and cellulase are formed. The sugars and cellulase are then fed into the fermentation vessel and the cellulase acts upon the cellulose from the main stream and converts it into the component sugars that in turn can be fermented to generate the fermentation product.

It is normally necessary to wash the solid by-product in order to ensure that it is substantially free of acid and in particular acetic acid which is used during the hydrolysis of hemicellulose. It is necessary to do this since the acetic acid or other impurities could poison the fungi used in the production of cellulase or the cellulase produced therefrom. Normally the wash water is recycled water, for instance water that has been separated from the still bottoms liquor in the distillation recovery of the fermentation product in which suspended solids have been removed.

Since the wash water may contain other impurities that could be harmful to either the cellulase, or fermentation processes it would be desirable to minimise the amount of wash water used.

A particular problem that can occur is that the efficiency of the process can be variable and sometimes resulting in diminished production of the fermentation product. There is a need to further improve the yield of fermentation product produced in this process and to increase the production rate.

Figure 1:
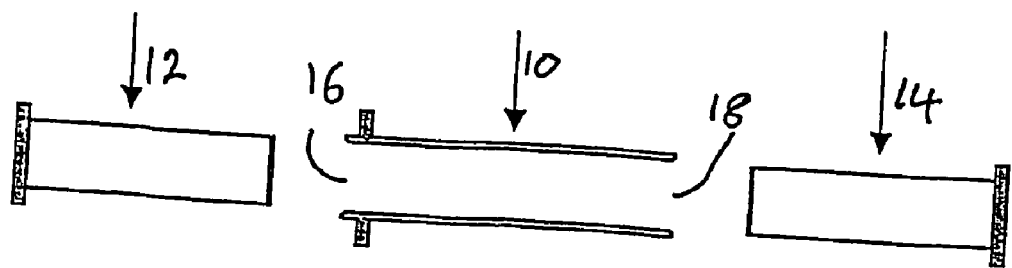
FIG. 1 is a diagrammatic axial section of a syringe.

According to the present invention we provide a process of producing fermentation product comprising the steps of, (i) forming an acidified suspension of particulate plant derived material comprising a first polysaccharide which is more readily hydrolysable and a second polysaccharide which is more difficult to hydrolyse, (ii) allowing the first polysaccharide to undergo hydrolysis by action of the acid at a temperature of at least 50° C. under conditions such that the first polysaccharide is hydrolysed and thereby forming a mixture of an aqueous liquor containing dissolved sugar and a solid residue containing the second polysaccharide, (iii) subjecting the mixture to one or more separation stages in which the solid residue and aqueous sugar liquor are substantially separated from each other, (iv) optionally washing the residue substantially free of acid and sugar, (v) adjusting the pH of the aqueous liquor to at least 4, (vi) passing the aqueous liquor from step (iv) into a fermentation stage where the dissolved sugars are acted upon by a microorganism in a fermentation broth to produce a fermentation product, (vii) contacting the second polysaccharide by an enzyme, said enzyme hydrolyses the second polysaccharide to the component sugars, and allowing the component sugars to be acted upon by a microorganism in the fermentation broth to produce the fermentation product, (viii) separating the fermentation product from the broth, characterised in that the separation stage(s) in step (iii) is/are assisted by flocculation of the solid by-product, employing one or more flocculating agent(s) selected from the group consisting of water-soluble or water-swellable natural, semi-natural and synthetic polymers and charged microparticulate materials.

We have found that surprisingly by using the special flocculation process in the separation stage, a consistently high yield of fermentation product can be achieved. It is thought that the residual acid and sugar in the solid residue feed interferes with the formation of the enzyme and the action of the enzyme on the second polysaccharide in the solid residue. This in turn results in incomplete conversion of the second polysaccharide into the component sugars, which in turn results in a reduced yield of fermentation product.

The improved separation stage in the process also has the advantage that the sugar solution resulting from the first hydrolysis stage is substantially free from extraneous solid material, such as cellulosic fibres.

According to the process of the present invention, the enzyme which acts on the second polysaccharide may be introduced directly into the solid by-product residue once it has been separated from the sugar liquor resulting from the hydrolysis of the first polysaccharide. or it may be added once the second polysaccharide has been introduced into the fermentation process. The enzyme may be introduced by allowing a fungus to grow on the second polysaccharide, in which the fungus generates an enzyme which hydrolyses the polysaccharide into its component sugars.

The fungus capable of producing suitable enzymes may be *Trichoderma reesei, Aspergillus niger, Humicola insolens* and *Thermnomonospora fusca*.

Alternatively the solid by-product containing the second polysaccharide is fed into the fermentation vessel and a commercially available enzyme is added directly into the fermentation vessel in order to act upon the second polysaccharide.

In one preferred form of the invention the solid residue of step (iv) comprising the second polysaccharide is divided into a main stream and a secondary stream. The main stream is passed directly into the fermentation stage, but the secondary stream of polysaccharide residue is passed into an enzyme production stage. In this stage the enzyme is generated by allowing fungi to act on the polysaccharide residue, and this results in the formation of enzyme and converts the second polysaccharide into its component sugars. The enzyme and resulting sugars are passed into the fermentation vessel. The enzyme process results in the production of sufficient enzyme to act upon the second polysaccharide introduced into the fermentation stage from the main stream. Therefore the second polysaccharide in the fermentation vessel is then hydrolysed to the component sugars.

Alternatively all of the solid residue of step (iv) comprising the second polysaccharide is passed to an enzyme treatment stage in which enzyme is generated by allowing fungi to grow on the polysaccharide. The enzyme hydrolyses the polysaccharide into the component sugars and then passing the sugars into the fermentation stage in which the sugars are converted into the fermentation product. However, the increasing concentration of sugars could inhibit the process of enzyme production and so it may be necessary to continually remove sugars that are formed.

The plant derived material is typically any readily available source of polysaccharides, particularly cellulosic materials. Typically the cellulosic material comprises materials selected from the group consisting of herbaceous biomass, softwood biomass, hardwood biomass, sewage sludge, paper mill sludge and the biomass fraction of municipal solid waste. The herbaceous biomass may for instance be bagasse, rice straw, rice hulls corn stover, wheat straw, grass, trees and cotton gin trash.

Preferably the plant derived material is cellulosic and comprises hemicellulose as the first polysaccharide and cellulose as the second polysaccharide. Generally the plant derived material also contains lignin or lignin type materials, which remain in the solid by-product.

The acidified suspension may be formed by combining a particulate material comprising cellulose, hemicellulose and lignin with a dilute acid. Alternatively the suspension can be made by treatment of a cellulosic biomass with sulphur dioxide gas, steam and water at an elevated temperature. Typically the process can be conducted by impregnation of the biomass material with $SO_2$ gas followed by steam at 205 to 215° C. for 5 minutes and then the addition of water to form a slurry (Stenberg et al., Recycling of Process Streams, Applied Biochemistry, Vol 70-72, 1998, page 697-707, 1998).

By dilute we mean that the acid generally has a concentration of less than 10% by weight. Usually though the concentration will be much lower, for instance less than 5%. The acid may be a strong mineral acid such as hydrochloric acid, sulphuric acid, sulphurous acid, hydrofluoric acid, nitric acid and phosphoric acid. Alternatively the acid may be an organic acid, for example carbonic acid, tartaric acid, glucuronic acid, formic acid, trichloroacetic acid or other carboxylic acids.

The acid ideally exhibits a pKa below 4. Preferred results are obtained by using either hydrochloric acid or sulphuric acid.

The hydrolysis of the first polysaccharide is preferably carried out at a temperature of between 120 and 220° C. for a period of 1 to 15 minutes, although lower temperatures are possible if the treatment time is longer.

In each of the first and second hydrolysis stages, the resulting hydrolysate is then separated from the solid materials, preferably through pressing of the treated material to separate the residue as a solid product. The solid product that is separated may be subjected to at least one wash cycle to remove any residual sugar solution from the solid. The wash cycle comprises washing the solid product with a suitable wash liquid. The wash liquid may be water. Normally the wash water is recycled water, for instance water that has been separated from the still bottoms liquor in the distillation recovery of the fermentation product in which suspended solids have been removed.

The liquid hydrolysate which contains sugars and acid can then be collected for further processing. When the first polysaccharide is hemicellulose, the resulting hydrolysate is generally $C_5$ sugars and when the second polysaccharide is cellulose the hydrolysate is generally $C_6$ sugars.

In each case it is important to adjust the pH of the acid sugar liquors to a pH value of at least 4. The pH adjustment may be done by addition of a base or by use of an ion exchange resin, which is capable of neutralising the acid. Preferably the pH of the acidified aqueous sugar liquor that results from the digestion process is adjusted to a pH of at least 10 by addition of a basic material such as sodium carbonate, and then subsequent adjustment of the pH to a more neutral or slightly acidic pH. Desirably the pH may be adjusted to a value of between 10 and 12, preferably about 11, by addition of a base, followed by titrating to pH 4 and 5, preferably about pH 4.5.

Alternatively the acid may be removed from the liquor by passing the hydrolysate through a bed of resin beads to remove the acid. The aqueous sugar stream that desirably contains at least 98% of the sugar present in the hydrolysate can then be recovered.

After the separation of the acid from the sugar stream, the acid is preferably concentrated for reuse for example by evaporation.

The fermentation process of the present invention typically involves allowing the fermentation to proceed for 3 to 5 days. Volatile fermentation products may be continually removed by recirculating carbon dioxide through a cooled condensing column. Desirably the fermentation products are collected from the condensing column after three to five days and then distilled. Preferably volatile fermentation products are separated from the broth by passing the broth comprising the fermentation product into a distillation stage, where the fermentation compound is collected as a distillate and the residue 'still bottoms' is removed. Microorganisms can be separated from the fermentation broth or preferably from the still bottoms, preferably through centrifugation and can be recycled for reuse. In one preferred aspect of the invention the fermentation product is separated from the broth by passing the broth comprising the fermentation product into a concentration stage, in which the fermentation compound is collected in the concentrate and extracted by at least one means selected from the group consisting of ion exchange, solvent extraction and electrodialysis.

The process can be used to prepare a range of fermentation products, but preferably the fermentation product is selected from the group consisting of ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid, tartaric acid and amino acids such as L-glutaric acid, L-lysine, L-aspartic acid, L-tryptophan, L-arylglycines or salts of any of these acids.

The microorganisms used in the fermentation process of the present invention can be, for example, a yeast such as *Klyveromyces* species, *Candida* species, *Pichia* species, *Brettanomyces* species, *Saccharomyces* species such as *Saccharomyces cerevisiae* and *Saccharomyces uvarum*, *Hansenula* species and *Pachysolen* species. Alternatively, the microorganism can be a bacterial species such as *Leuconostoc, Enterobacter, Klebsiella, Erwinia, Serratia, Lactobacillus, Lactococcus, Pediococcus, Clostridium, Acetobacter, Gluconobacter, Lactobacillus, Aspergillus, Propionibactedum, Rhizopus* and *Zymomonas mobils*. In addition genetically modified strains may also be used.

Since the solid product generally comprises lignin and analogous materials it can be particularly difficult to separate from the liquor. We have unexpectedly found that the production of fermentation product can be significantly improved by applying one or more flocculatings agent to the separation of the hydrolysate from the solid product. We have found that the solid product can be more efficiently dewatered by the process and that a higher cake solids can be achieved. Since the solid product can be more efficiently dewatered there is a reduced requirement for separation equipment capacity and equipment that is less capital intensive and less expensive to operate, such as a filter press, can be used. Since higher cake solids can be achieved, less of the acid sugar solution remains in the residual by-product solid. Hence the quantity of water required to wash the by-product solid free of acid and sugar is much reduced, improving both the productivity and efficiency of the process.

Suitably the flocculating agent is selected from the group consisting of water soluble or water swellable natural, semi-natural and synthetic polymers. Preferably the polymer is synthetic and may be formed by polymerisation of at least one cationic, non-ionic or and/or anionic monomer(s) alone or with other water soluble monomers. By water soluble we mean that the monomer has a solubility of at least 5 g/100 ml at 25° C.

Preferably polymeric flocculating agents are formed from ethylenically unsaturated water soluble monomers that readily polymerise to produce high molecular weight polymers. Particularly preferred polymers include monomers that are selected from the group consisting of polyacrylate salts, polyacrylamide, copolymers of acrylamide with (meth) acrylic acid or salts thereof, copolymers of acrylamide with dialkylaminoalkyl (meth) acrylate or acid addition or quatemary ammonium salts, polymers of diallyidimethyl ammonium chloride, polyamines and polyethylene imines. The polymers may be linear, branched or cross-linked.

The polymers may be prepared by any convenient conventional process, for instance by solution polymerisation, gel polymerisation, reverse phase suspension polymerisation and reverse phase emulsion polymerisation. Suitable processes include those described in EP-A-150933 or EP-A-102759.

Suitable polymers are anionic, cationic and non-ionic polymers. The preferred polymers are non-ionic and cationic polymers of sufficiently high molecular weight such that it exhibits an intrinsic viscosity of at least 4 dl/g. Such an intrinsic viscosity generally indicates a polymer of several million molecular weight, for instance generally greater than 5,000,000 and usually at least 7,000,000. In general the polymer preferably has an intrinsic viscosity greater than 6 dl/g, often at least 8 or 9 dl/g. The intrinsic viscosity can be as high as 30 dl/g or higher. In many cases though suitable cationic polymers exhibit an intrinsic viscosity in the range of 7 to 25 dl/g, in particular 10 to 20 dl/g, in particular around 14 or 15 dl/g.

Suitable cationic monomers include quaternary ammonium or acid salts of monomers which contain amine groups. Preferably the cationic polymer is formed from a monomer or blend of monomers comprising at least one cationic monomer selected from the group consisting of quaternary ammonium and acid salts of dimethylaminoethyl (meth) acrylate, quaternary ammonium and acid salts of dimethylaminoethyl (meth) acrylamide and diallyldimethyl ammonium chloride. The cationic monomers may be hompolymerised or copolymerised with other monomers, for instance acrylamide. The cationic polymers thus may be any polymer that carries a cationic, provided of course that they are of sufficiently high molecular weight to exhibit an intrinsic viscosity of at least 4 dl/g. Intrinsic viscosity is measured using a suspended level viscometer in 1 M NaCl buffered to pH 7.5 at 25° C.

The cationic polymers according to the invention may be prepared as substantially linear polymers or as branched or structured polymers. Structured or branched polymers are usually prepared by inclusion of polyethylenically unsaturated monomers, such as methylene-bis-acrylamide into the monomer mix, for instance as given in EP-B-202780. Preferably however, the polymers are substantially linear and are prepared in the form of a bead or powdered product.

Suitably the polymeric flocculating agent would be added as an aqueous solution or aqueous dispersion. The polymer may be added in an amount sufficient to effect flocculation. Typically the amount of polymeric flocculating agent sufficient to induce flocculation would be usually at least 0.002 weight % based on weight of suspended solids. Usually better flocculation and therefore separation can be achieved if at least 0.01% is used. The dose may be substantially higher, for instance up to 1%. However, optimum flocculation and separation is normally achieved using doses in the range of 0.015% to 0.2%, especially 0.02% to 0.1%. Following flocculation of the suspended solids the solid product can be separated from the hydrolysate aqueous liquor by mechanical means, for instance filter press, centrifuge, belt press, horizontal belt filter or pressure filter. The action of the flocculating agent greatly enhances the separation of the solids from the liquor by comparison to separation using solely mechanical means. We have found that the process of the present invention provides a higher cake solids, with less trapped residual aqueous liquor, which means that a higher proportion of the sugar liquor is available for conversion into the fermentation product. Likewise we find that the aqueous liquor contains much lower levels of extraneous suspended cellulosic solids. Furthermore we also find that less wash water is required.

The solid product that results from the separation step should be as dry as possible in order to prevent any loss of sugar, which would otherwise be used in the fermentation process.

In a further preferred embodiment of the present invention the flocculating agent is a charged microparticulate material. Particularly suitable examples of charged microparticulate materials include swellable clays, anionic, cationic or amphoteric microparticulate silica based materials and organic cross-linked polymeric microparticles.

The siliceous material may be any of the materials selected from the group consisting of silica based particles, silica microgels, colloidal silica, silica sols, silica gels, polysilicates, aluminosilicates, polyaluminosilicates, borosilicates, polyborosilicates, zeolites or swellable clay.

This siliceous material may be in the form of an anionic microparticulate material. Alternatively the siliceous material may be a cationic silica. Desirably the siliceous material may be selected from silicas and polysilicates.

The polysilicates of the invention may be prepared by reducing the pH of an aqueous solution of an alkali metal silicate. For instance polysilicic microgels otherwise known as active silica may be prepared by acidification of alkali metal silicate to between pH 2 and 10 by use of mineral acids or acid exchange resins, acid salts and acid gases. It may be desired to age the freshly formed polysilicic acid in order to allow sufficient three dimensional network structure to form.

Generally the time of ageing is insufficient for the polysilicic acid to gel. Particularly preferred siliceous material include polyalumino-silicates. The polyaluminosilicates may be for instance aluminated polysilicic acid, made by first forming polysilicic acid microparticles and then post treating with aluminium salts.

Alternatively the polyaluminosilicates may be polyparticulate polysicilic microgels of surface area in excess of 1000 m$^2$/g formed by reacting an alkali metal silicate with acid and water soluble aluminium salts. Typically the polyaluminosilicates may have a mole ratio of alumina:silica of between 1:10 and 1:1500.

Polyaluminosilicates may be formed by reducing the pH of an aqueous solution of alkali metal silicate to between pH 2 and 10 using concentrated sulphuric acid containing 0.2 to 2.0% by weight of a water soluble aluminium salt, for instance aluminium sulphate. The aqueous solution may be aged sufficiently for the three dimensional microgel to form. Typically the polyaluminosilicate is aged for up to about two and a half hours before diluting the aqueous polysilicate to 0.5 weight % of silica.

The siliceous material may be a colloidal borosilicate. The colloidal borosilicate may be prepared by contacting a dilute aqueous solution of an alkali metal silicate with a cation exchange resin to produce a silicic acid and then forming a heel by mixing together a dilute aqueous solution of an alkali metal borate with an alkali metal hydroxide to form an aqueous solution containing 0.01 to 30% $B_2O_3$, having a pH of from 7 to 10.5.

The swellable clays may for instance be typically a bentonite type clay. The preferred clays are swellable in water and include clays which are naturally water swellable or clays which can be modified, for instance by ion exchange to render them water swellable. Suitable water swellable clays include but are not limited to clays often referred to as hectorite, smectites, montmorillonites, nontronites, saponite, sauconite, hormites, attapulgites and sepiolites.

Most preferably the clay is a bentonite type clay. The bentonite may be provided as an alkali metal bentonite. Bentonites occur naturally either as alkaline bentonites, such as sodium bentonite or as the alkaline earth metal salt, usually the calcium or magnesium salt. Generally the alkaline earth metal bentonites are activated by treatment with sodium carbonate or sodium bicarbonate. Activated swellable bentonite clay is often supplied as a dry powder. Alternatively the bentonite may be provided as a high solids flowable slurry, for example at least 15 or 20% solids.

When the charged microparticulate material comprises an organic cross-linked polymeric microparticles. The microparticles may be made as microemulsions by a process employing an aqueous solution comprising a cationic or anionic monomer and crosslinking agent; an oil comprising a saturated hydrocarbon; and an effective amount of a surfactant sufficient to produce particles of less than about 0.75 micron in unswollen number average particle size diameter.

Microbeads are also made as microgels by procedures described by Ying Huang et. al., Makromol. Chem. 186, 273-281 (1985) or may be obtained commercially as microlatices. The term "microparticle", as used herein, is meant to include all of these configurations, i.e. beads per se, microgels and microlatices.

The charged microparticle material may be used in amounts of at least 0.002% based on weight of suspended solids. Typically though the doses are usually as high as 0.8 or 1.0% or higher. When the charged microparticle material is inorganic, the dose is usually in excess of 0.06%, preferably in the range 0.1 to 0.6%. When the charged microparticle is organic the dose is typically below 0.3%, preferably in the range 0.02 to 0.1%.

Unexpectedly we have found that the hydrolysate liquor can be separated particularly rapidly when the flocculation is effected by employing a water-soluble or water-swellable polymer and a charged microparticulate material. In one aspect we find that particularly effective flocculation and separation of the solids from the liquor is achieved when flocculation is carried out by introducing an anionic microparticle material into the mixture and then reflocculating by adding a cationic or substantially non-ionic polymer. In a further preferred embodiment of the present invention we find that especially fast and efficient separation of solids is achieved by a process in which flocculation is effected by introducing a cationic polymer into the mixture and then reflocculating by adding an anionic microparticulate material.

The following examples illustrate the invention.

EXAMPLE 1

Pre-hydrolysis: Milled wood chips steamed with low pressure steam to approximately 100C. After steaming concentrated sulphuric acid is diluted and added to the mixture until the mixture contains 0.52% acid and the solids in the reactor are 22% by weight. The mixture is then steam heated to 175°

C. for 15 minutes. The mixture is then flash cooled for 15 minutes to remove 6.5% of the acetic acid and 61% of the furfural and hydroxymethyl furfural.

Separation: The 26% insoluble solids present in the pre-hydrolysed slurry (containing 0.38% sulphuric acid) is then separated on a filter press. Prior to pressing solutions of flocculant or flocculants (at 0.2 to 0.5% solids) and/or particulate suspensions (at 0.2 to 0.5% solids) are added into the feed stream with necessary agitation at a dose of 0.22 to 2 Kg per tonne of solids. Flocculants increase the rate of free drainage by gravity through a porous belt, before preparation of a filter cake in a wedge zone and subsequent further dewatering in a pressure zone. A method of reducing the toxins remaining in the liquid portion is to wash with (recycled) water.

After ion exchange for the removal of acetic acid, the liquid portion of the hydrolysate is acidified to pH 2 by the addition of sulphuric acid. Lime is then added to raise the pH to 10 and the liquor is then heated to 50° C. The liquid is then adjusted to the fermentation pH of 4.5 for 4 hours allowing gypsum crystals to form for separation by filtration.

Simultaneous Saccharification and Co-Fermentation (SSCF): Detoxified and diluted hydrolysed solids is split to cellulase fermentations, Z. mobilis seed production and SSCF fermenters. The hydrolysate feed stream is 22% combined soluble and insoluble solids. The portion of hydrolysed solid residue is that is split off for Z. mobilis seed production is approximately 10%. The portion of hydrolysate split off for cellulase production is dependent on both the cellulase yield on the xylose and cellulose present and the required loading of enzyme in the SSCF. For cellulase production pre-hydrolysed solids-conditioned hydrolysate liquor, recycled water, corn steep liquor (to 1%) and nutrients (($NH_4)_2SO_4$, $KH_2PO_4$, $MgSO_4.7H_2O$ $CaCl_2.2H_2O$ and Tween 80) and corn oil as an antifoam (0.1% v/v) are combined to give a final cellulose concentration of 4%. The batch is then run for 160 hours at 28° C. to produce cellulase. For SSCF, detoxified hydrolysate slurry (22% total solids) is cooled to 30° C. and added to the fermenter together with a 10%(v/v) seed inoculum. Corn steep liquor is added to 0.25% and cellulase to give a final concentration of 15 FPU/g cellulose and an initial cellulose concentration of 22%. The SSCF fermentation in which cellulose is converted to fermentable sugars by cellulase and the fermentable sugars converted to ethanol by Z. mobilis takes 7 days.

EXAMPLE 2

Pre-hydrolysis: Softwood chips (2 mm) with a dry solids content of 48% were added to 400 g of water and heated to 190° C. Once at 190° C. sulphuric acid was added to a concentration of 0.7% under nitrogen pressure and the mixture was left for 3 minutes. The temperature was rapidly reduced to 80° C. and the insoluble solids present in the pre-hydrolysed slurry (containing 0.32% sulphuric acid) was then separated on a filter press. Prior to pressing, solutions of flocculant or flocculants (at 0.2 to 0.5% solids) and/or particulate suspensions (at 0.5 to 15% solids) are injected into the slurry with necessary agitation at a dose of 0.2 to 2 Kg per tonne of solids.

Enzymic hydrolysis: Tap water is added to the recovered pre-hydrolysesd solid matter to adjust the dry matter content of the suspension to 7.5% (w/w). The pH was adjusted to 4.8 with calcium hydroxide and then 10% (w/w) sodium hydroxide was used to maintain the pH at 4.8 during hydrolysis. To perform the hydrolysis cellulase (activity 75 FPU/g), was added at a dose of 0.175g/g of fibrous material supplemented with 0.025 g/g cellobiase (β-galactosidase activity 400 IU/g).

Hydrolysis was allowed to proceed for 4 days. The solid residues were then separated in a filter press. Prior to pressing solutions of flocculant or flocculants (at 0.2 to 0.5% solids) or particulate suspensions (at 0.5 to 15% solids) are added into the slurry with necessary agitation at a dose of 2 to 10 Kg per tonne of solids.

fermentation: The hydrolysate was supplemented to a final concentration of 0.5 g/L $(NH_4)_2SO_4$ and 0.025 g/L $MgSO_4.7H_2O$ and inoculated with yeast to a concentration of 1% (w/v). The fermentation was maintained at 30° C. and at pH 4.8 by the addition of 10% (w/w) sodium hydroxide.

EXAMPLE 3

Figure 2:
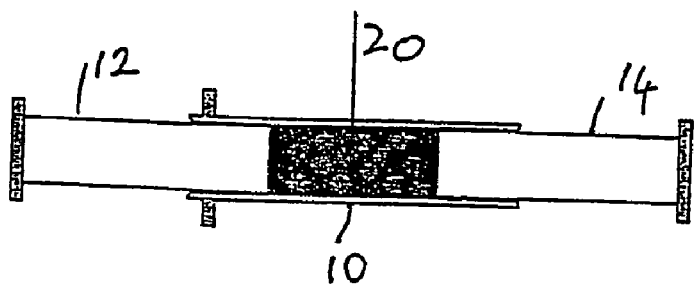
FIG. 2 shows the syringe of FIG. 1 containing a sample to be tested.
Figure 3:
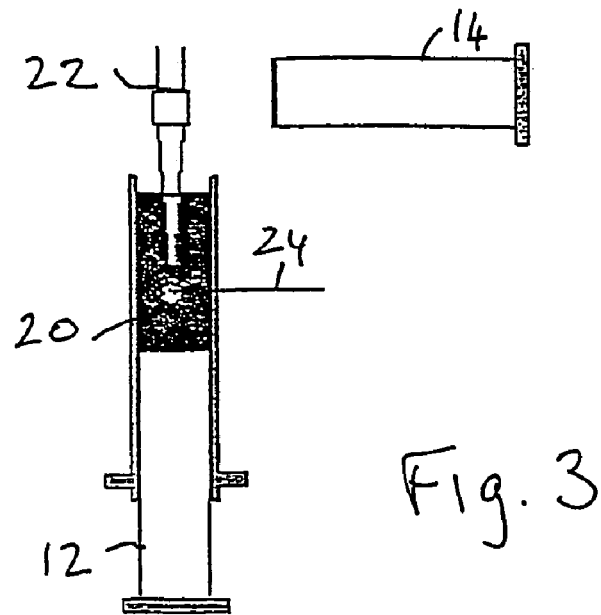
FIG. 3 illustrates the introduction of flocculant into the sample.
Figure 4:
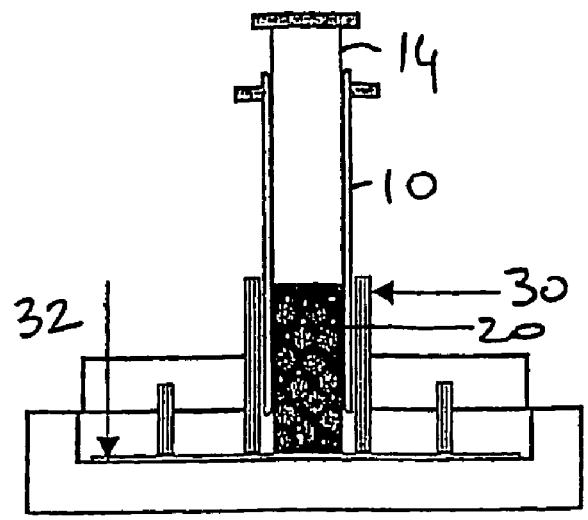
FIG. 4 shows a test rig in part sectional side elevation.
Figure 5:
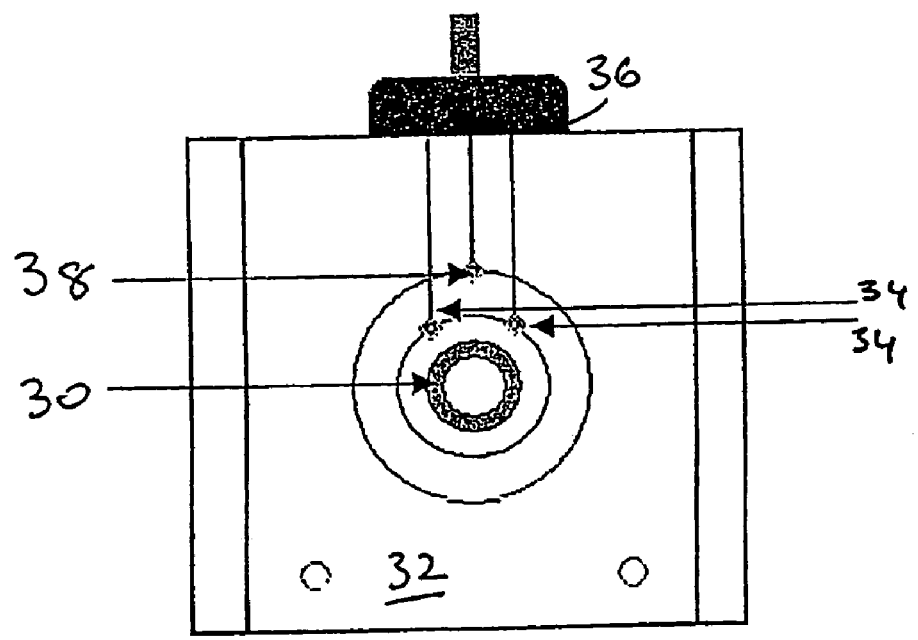
FIG. 5 is a part sectional plan view of the rig of FIG. 4.
Figure 6:
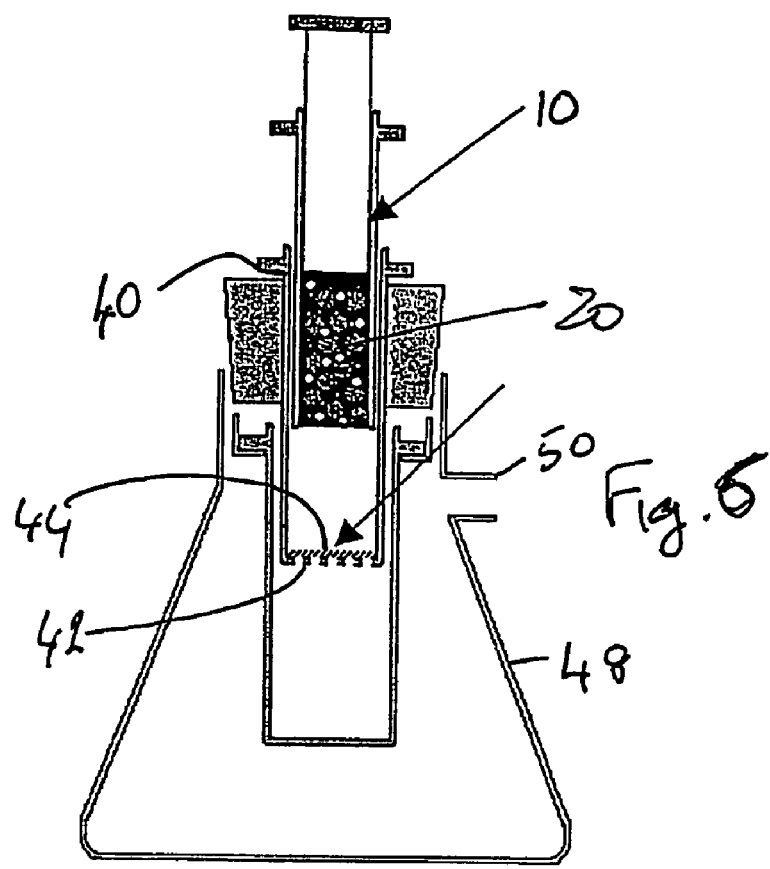
FIGS. 6 and 7 are vertical sections through a device for separating liquid from the sample.
Figure 7:
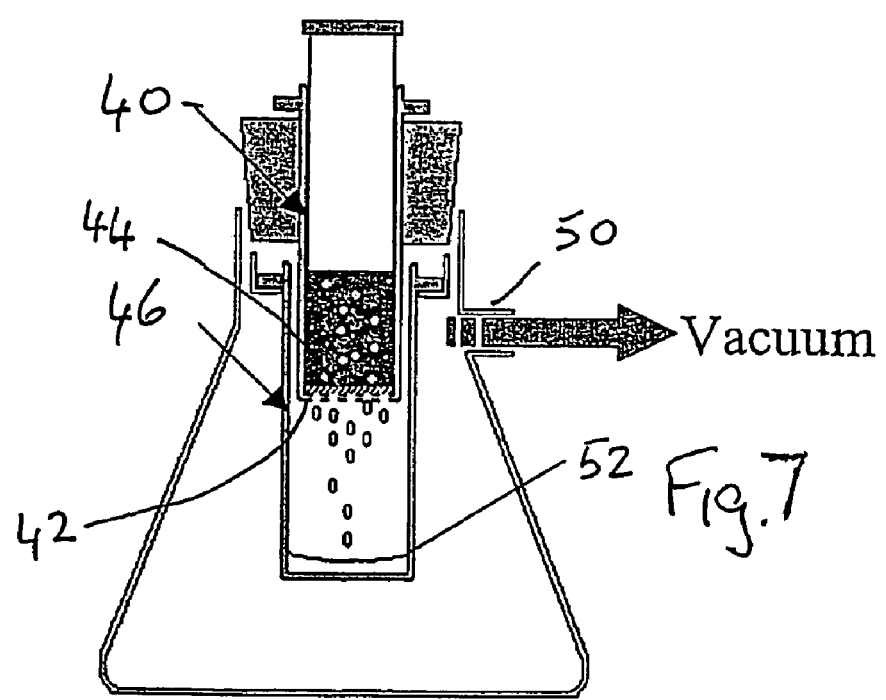
Figure 8:
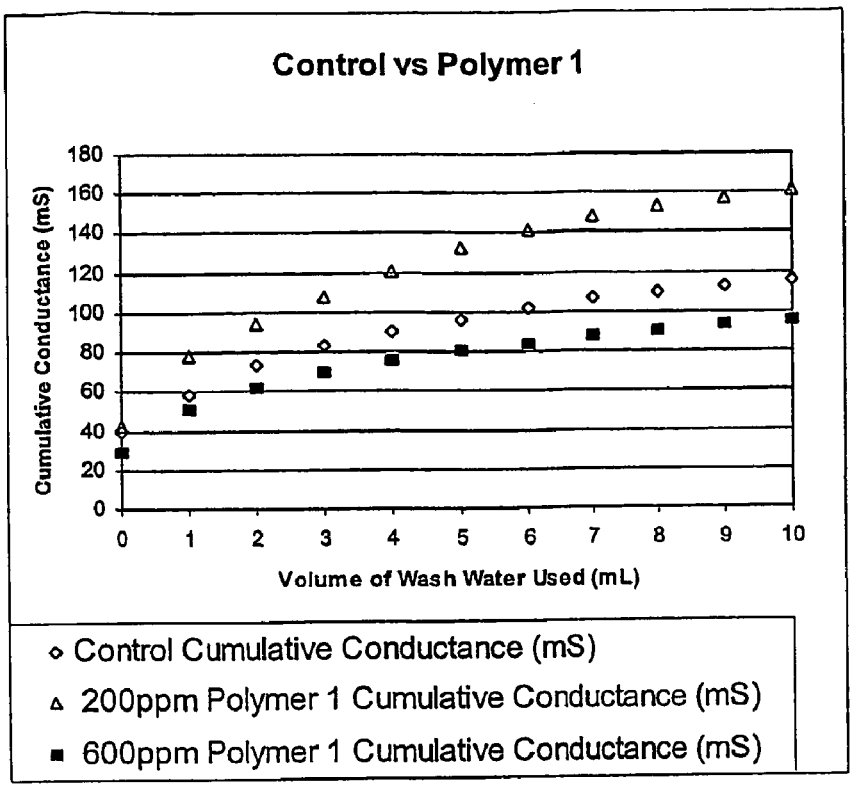
FIG. 8 is a graph showing the cumulative conductance, which arises from removal of the acid in the separated liquid
Figure 9:
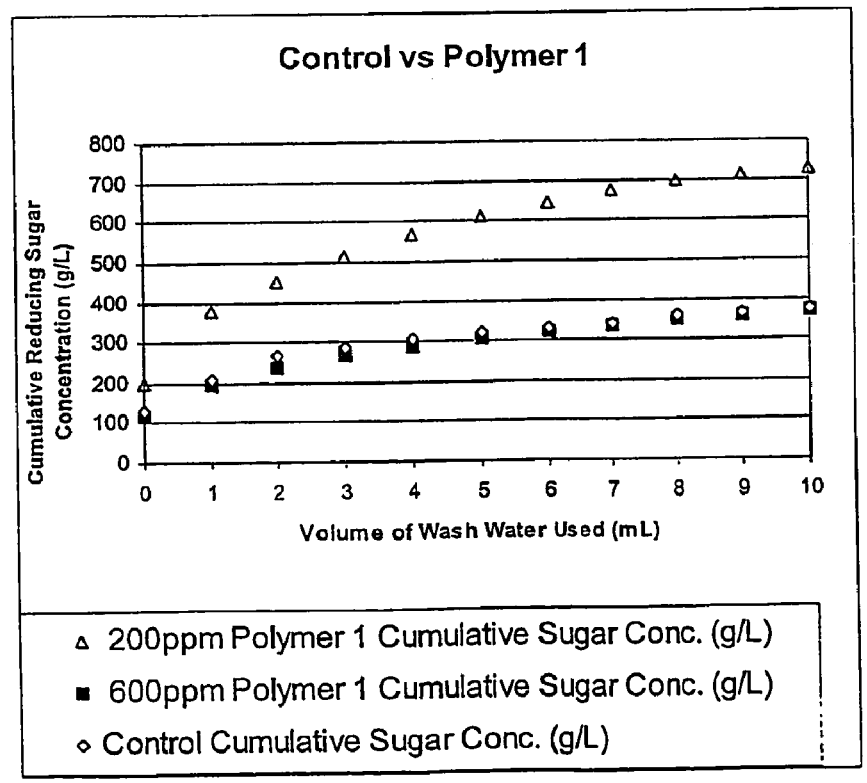
FIG. 9 is a graph of the cumulative amount of sugar removed in the separated liquid.

The separation of acid and sugar from the fermantation product of the invention was assessed using the equipment and the results obtained will now be described by way of example in the accompanying drawings in which:

FIG. 1 is a diagrammatic axial section of a syringe,

FIG. 2 shows the syringe of FIG. 1 containing a sample to be tested,

FIG. 3 illustrates the introduction of flocculant into the sample,

FIG. 4 shows a test rig in part sectional side elevation,

FIG. 5 is a part sectional plan view of the rig of FIG. 4,

FIGS. 6 and 7 are vertical sections through a device for separating liquid from the sample, FIG. 8 is a graph showing the cumulative conductance, which arises from removal of the acidin the separated liquid and FIG. 9 is a graph of the cumulative amount of sugar removed in the separated liquid.

Referring to FIG. 1 of the drawings an open ended syringe housing 10 of circular cross section is adapted to receive syringe plungers 12 and 14 into each open end 16 and 18 respectively. As shown in FIG. 2 a sample 20 of hydrolysate to be examined, optionally together with some ball bearings, is disposed in the syringe housing substantially in the mid part thereof and held in place by the plungers 12 and 14. The syringe together with the sample is incubated for a period of time, for example 15 minutes at a temperature which is typically about 90° C. After incubation one plunger is removed from the syringe and as shown in FIG. 3 polymer flocculant 24 is introduced into the sample with a pipette 22. The removed plunger is replaced and the syringe shaken in order to try to ensure that the polymer is distributed throughout the sample. The syringe is then incubated again for example for about ten minutes at a temperature of, for example, 90° C.

The speed at which liquid separates from the solids In the sample can now be measured using the rig shown in FIGS. 4 and 5. This consists of a vertically oriented tube 30 sized to receive the syringe at its upper end. The lower end of tube 30 is disposed just above a filter paper 32. Contacts 34 are provided adjacent the filter paper which are arranged to supply a signal to a timer 36 to start the timer when liquid spreads to the contacts 34 from the tube. A further contact 38 linked to the timer is arranged to turn the timer off when liquid from the tube reaches contact 38. Thus the rig measures the time taken for liquid to spread across the filter paper from contact 34 to contact 38. This is known as Capillary Suction Time (CST) and is measure of the speed of separation of liquid from solids in the test sample.

To obtain the CST for the sample one plunger is removed and the syringe is inserted into the tube 30, the other plunger being moved into the syringe housing to bring the sample into contact with the filter paper 32 as Illustrated in FIG. 4. Liquid separating from the sample spreads across the filter paper outwardly from the area of contact of the sample with the filter paper starting the timer when it reaches contacts 34 and stopping the timer when it reaches contact 38.

Using the above described equipment the CST was determined for 5 g. samples of hydrolysate flocculant polymer being added as shown in the following table: The target CST was 98.8.

| Polymer Addition | CST seconds |
|---|---|
| Control + 100 μl H$_2$O | 127.9 |
| 100 μl Polymer 1 | 91.8 |

Polymer 1 is an acrylamide homopolymer with an IV of approx 15 dl/g.

EXAMPLE 4

Following the procedure described with reference to FIGS. 1 to 3 after the second incubation one of the plungers is removed from the syringe and as shown in FIGS. 6 and 7 the open end of the syringe inserted into the open top of a larger syringe 40 having a perforated base 42 for supporting a mesh 44. A receiving cylinder 46 is positioned around the lower end of syringe 40 and the assembly of syringe 40 and cylinder 46 is mounted in flask 48 having a connection 50 to a vacuum. The sample is washed and filtrate 52 collecting in the receiving cylinder can be examined.

The equipment with reference to FIGS. 6 and 7 was used to examine the separation of acid and sugar from a sample of hydrolysate treated in accordance with invention.

A 5 g sample of hydrolysate derived from corn stover was placed in the syringe housing 10 together with some ball bearings and held in place with the plungers during Incubation. 0.1 ml of a 1% solution of Polymer 1 was introduced into the sample by a pipette as illustrated in FIG. 2. After the second incubation the sample and flocculant was transferred from syringe housing 10 to syringe 40, a 58 micron mesh having been provided on the perforated base 42. 10 ml of wash water was delivered to the syringe 40 while the vacuum was applied. The conductance of the filtrate was measured for each 1 ml of liquid recovered and the cumulative conductance results are shown on the graph of FIG. 8 which also shows the results obtained from a control sample. As can be seen the inclusion of the flocculant caused a rapid increase in the conductance on the addition of the wash water which indicates that acid is being removed.

FIG. 9 shows the increase in sugar concentration in the filtrate with the addition of wash water.

EXAMPLE 5

Following the same procedure as in Example 4 the actual amount of sugar recovered was evaluated with two different polymers at two different polymer concentrations. The tests were performed twice at each concentration and the results shown in the following Table 1.

| | Polymer Concentration | | | |
|---|---|---|---|---|
| | 200 ppm | | 600 ppm | |
| Control | 190 mg | 181 mg | 249 mg | 237 mg |
| | 7.8 mls | 7.4 mls | 8.3 mls | 7.8 mls |
| Polymer 2 | 211 mg | 200 mg | 257 mg | 244 mg |
| | 7.4 mls | 7.0 mls | 8.1 mls | 7.7 mls |
| Polymer 1 | 386 mg | 367 mg | 246 mg | 233 mg |
| | 7.2 mls | 6.8 mls | 8.9 mls | 8.5 mls |

Polymer 2 is a copolymer or 8% sodium acrylate 92% acrylamide, IV approx 9 dl/g

The above results are based on recovery of about 95% of the wash water. Recalculating the figures on the theoretical basis that all 10 mls of the wash water is recovered the results are as follows:

| | Polymer Concentration | | | |
|---|---|---|---|---|
| | 200 ppm | | 600 ppm | |
| Control | 243 mg | 231 mg | 300 mg | 285 mg |
| Polymer 2 | 285 mg | 271 mg | 317 mg | 301 mg |
| Polymer 1 | 536 mg | 509 mg | 276 mg | 262 mg |

The invention claimed is:

1. A process of producing fermentation product comprising the steps of,
   (i) forming an acidified suspension of particulate plant derived material comprising a first polysaccharide which is more readily hydrolysable and a second polysaccharide which is more difficult to hydrolyse,
   (ii) allowing the first polysaccharide to undergo hydrolysis by action of an acid at a temperature of at least 50° C. under conditions such that the first polysaccharide is hydrolysed and thereby forming an acidic mixture of an aqueous liquor containing dissolved sugar and a solid residue containing the second polysaccharide,
   (iii) subjecting the acidic mixture to one or more separation stages in which the solid residue and aqueous sugar liquor are substantially separated from each other,
   (iv) optionally washing the residue substantially free of acid and sugar,
   (v) adjusting the pH of the aqueous liquor to at least 4,
   (vi) passing the aqueous liquor from step (v) into a fermentation stage where the dissolved sugars are acted upon by a microorganism in a fermentation broth to produce a fermentation product,
   (vii) contacting the second polysaccharide by an enzyme, said enzyme hydrolyses the second polysaccharide to the component sugars, and allowing the component sugars to be acted upon by a microorganism in the fermentation broth to produce the fermentation product,
   (viii) separating the fermentation product from the broth, characterised in that the separation stage(s) in step (iii) is/are assisted by flocculation of the solid residue, employing one or more flocculating agent(s) selected from the group consisting of water-soluble polymers, water-swellable polymers and charged microparticulate material, wherein said one or more separation stages include a mechanical means selected from the group consisting of a filter press, centrifuge, belt press, horizontal belt filter, and pressure filter, and said solid residue includes cake solids.

2. A process according to claim 1 in which the solid residue of step (iv) comprising the second polysaccharide is divided into a main stream and a secondary stream, and passing the main stream directly into the fermentation stage, wherein the secondary stream of polysaccharide residue is passed into an enzyme production stage, in which enzyme is generated by allowing fungi to act on the polysaccharide residue, resulting in the formation of enzyme and sugars resulting from the second polysaccharide contained within the secondary stream, then passing the enzyme and sugars of step (vi) into the fermentation stage, wherein the enzyme acts on the second polysaccharide in the fermentation vessel and hydrolyses the second polysaccharide to the component sugars.

3. A process according to claim 1 in which the solid residue of step (iv) comprising the second polysaccharide is passed to an enzyme treatment stage in which enzyme is generated by allowing fungi to grow on the polysaccharide and said enzyme hydrolyses the polysaccharide into the component sugars and then passing the resulting sugars into the fermentation stage in which the sugars are converted into the fermentation product.

4. A process according to claim 1 in which the plant derived material comprises materials selected from the group consisting of herbaceous biomass, softwood biomass, hardwood biomass, sewage sludge, paper mill sludge and the biomass fraction of municipal solid waste.

5. A process according to claim 1 in which the plant derived material is cellulosic and comprises hemicellulose as the first polysaccharide and cellulose as the second polysaccharide.

6. A process according to claim 1 in which the acid has a pKa of below 4 and has a concentration up to 2% by weight.

7. A process according to claim 1 in which the acid is selected from the group consisting of sulphuric acid and hydrochloric acid.

8. A process according to claim 1 in which the hydrolysis of the first polysaccharide is conducted at a temperature of between 120 to 220° C. for a period of from 1 minute to 15 minutes.

9. A process according to claim 1 in which the flocculating agent is selected from the group consisting of water soluble or water swellable natural, semi-natural and synthetic polymers.

10. A process according to claim 9 in which the polymer is formed from a water soluble monomer or blend of monomers.

11. A process according to claim 9 in which the polymer is selected from the group consisting of polyacrylate salts, polyacrylamide, copolymers of acrylamide with (meth) acrylic acid or salts thereof, copolymers of acrylamide with dialkylaminoalkyl (meth) acrylate or acid addition or quaternary ammonium salts, polymers of diallyldimethyl ammonium chloride, polyamines and polyethylene imines.

12. A process according to claim 1 in which the flocculating agent is a charged microparticulate material.

13. A process according to claim 12 in which the charged microparticulate material is selected from the group consisting of swellable clays, anionic, cationic or amphoteric microparticulate silica based materials and organic cross-linked polymeric microparticles.

14. A process according to claim 1 in which flocculation is effected by employing a water soluble or water-swellable polymer and a charged microparticulate material.

15. A process according to claim 1 in which flocculation is effected by introducing an anionic microparticle material into the mixture and then reflocculating by adding a substantially non-ionic polymer.

16. A process according to claim 1 in which flocculation is effected by introducing a cationic polymer into the mixture and then reflocculating by adding an anionic microparticulate material.

17. A process according to claim 1 in which flocculation is effected by introducing a cationic polymer into the mixture and then reflocculating by adding an anionic polymer.

18. A process according to claim 1 in which flocculation is effected by introducing an anionic polymer into the mixture and then reflocculating by adding a cationic polymer.

19. A process according to claim 1 in which the solid residue comprises lignin.

20. A process according to claim 1 in which the fermentation product is selected from the group consisting of ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid, tartaric acid and amino acids wherein the amino acids are selected from the group consisting of L-glutaric acid, L-lysine, L-aspartic acid, L-tryptophan, L-arylglycines and salts of any of these acids.

21. A process according to claim 1 in which the fermentation product is separated from the broth by passing the broth comprising the fermentation product into a distillation stage, where the fermentation compound is collected as a distillate and the residue 'still bottoms' is removed.

22. A process according to claim 1 in which the fermentation product is separated from the broth by passing the broth comprising the fermentation product into a concentration stage, in which the fermentation product is collected in the concentrate and extracted by at least one means selected from the group consisting of ion exchange, solvent extraction and electrodialysis.

\* \* \* \* \*